United States Patent
Bowman

[11] 4,092,330
[45] May 30, 1978

[54] 1,4-OXAZEPINES

[75] Inventor: Robert Mathews Bowman, Summit, N.J.

[73] Assignee: Ciba-Geigy Corporation, Ardsley, N.Y.

[21] Appl. No.: 734,075

[22] Filed: Oct. 20, 1976

Related U.S. Application Data

[60] Division of Ser. No. 615,255, Sep. 22, 1975, Pat. No. 4,010,166, which is a continuation-in-part of Ser. No. 526,758, Nov. 25, 1974, Pat. No. 3,988,448.

[51] Int. Cl.² ............................................ C07D 269/00
[52] U.S. Cl. ..................................... 260/333; 424/244
[58] Field of Search ........................................ 260/333

*Primary Examiner*—Norma S. Milestone
*Attorney, Agent, or Firm*—Theodore O. Groeger

[57] ABSTRACT

7,7-Diphenyl-hexahydro-1,4-oxazepines, e.g. those of the formula:

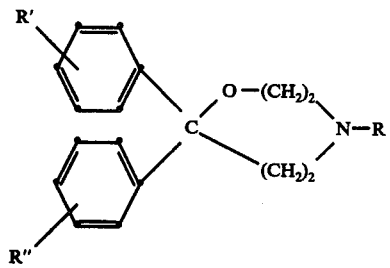

R = H, aliphatic, cycloaliphatic, araliphatic or aromatic radical

R',R" = H, alkyl, OH, alkoxy, alkylmercapto, halogen or $CF_3$ acyl derivatives, N-oxides and salts thereof are antidepressants.

6 Claims, No Drawings

1,4-OXAZEPINES

CROSS-REFERENCE TO RELATED APPLICATION

This is a division of copending application Ser. No. 615,255, filed Sept. 22, 1975 (now Pat. No. 4,010,166), which, in turn, is a continuation-in-part of application Ser. No. 526,758, filed Nov. 25, 1974 (now U.S. Pat. No. 3,988,448).

SUMMARY OF THE INVENTION

The present invention concerns and has for its object the provision of new 7,7-diphenyl-hexahydro-1,4-oxazepines, more particularly of those corresponding to Formula I

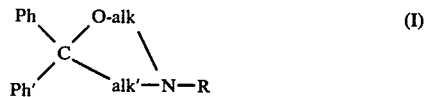

wherein each of alk and alk' is lower alkylene separating the adjacent atoms by 2 carbon atoms, R is lower alkyl, alkenyl, alkynyl, (cycloalkyl, cycloalkenyl, Ph or Hc)—$C_mH_{2(m-q)}$, (PhCO, CN, carboxy or carbalkoxy)—$C_nH_{2n}$, (hydroxy, halogeno, amino, mono- or dialkylamino)—$C_pH_{2p}$, halogeno—$C_pH_{2p-2}$, lower alkanoyl, alkenoyl, alkoxycarbonyl, (cycloalkyl, cycloalkenyl, Ph or Hc)—$C_mH_{2m}$—CO or (halogeno or di-lower alkylamino)—$C_pH_{2p}$—CO; each of Ph and Ph' is phenyl, unsubstituted or substituted by up to three members of lower alkyl, alkoxy, alkylmercapto, hydroxy, halogeno or trifluoromethyl; Hc is furyl, thienyl or pyridyl, unsubstituted or substituted by up to three lower alkyls; $m$ is an integer from 0 to 4; $n$ such from 1 to 4; $p$ such from 2 to 4; $q$ such from 0 to 2 and $(m-q)$ is positive; or the N-oxide of said tertiary nitrogen compounds or a therapeutically acceptable acid addition salt thereof; of corresponding pharmaceutical compositions and of methods for the preparation and application of these products, which are useful antidepressant agents.

DESCRIPTION OF THE PREFERRED EMBODIMENTS

A lower alkylene group alk and alk' is preferably ethylene, but also, for example, 1,2-propylene or -butylene.

A lower alkyl, alkenyl or alkynyl group R is preferably methyl, ethyl, n- or i-propyl or -butyl; allyl, methallyl, 2- or 3-butenyl or 3-methyl-2-butenyl; propargyl, 2- or 3-butynyl. A lower cycloalkyl or cycloalkenyl group is 3 to 7 ring-membered or 5 to 7 ring-membered respectively, such as cyclopropyl, cyclobutyl, cyclopentyl or cyclohexyl; 1-, 2- or 3-cyclopentenyl or -cyclohexenyl.

Of the radicals Ph and Ph' one is preferably phenyl and the other phenyl, (lower alkyl)-phenyl, mono-, di- or tri-(lower alkoxy)-phenyl, (lower alkylmercapto, hydroxy, halogeno or trifluoromethyl)-phenyl, wherein alkyl has been illustrated above and preferably represents methyl, lower alkoxy or alkylmercapto are preferably methoxy or methylmercapto, but also ethoxy, n- or i-propoxy or -butoxy or ethylmercapto respectively, and halogeno is preferably fluoro, chloro or bromo. A carbalkoxy group is preferably carbomethoxy or carbethoxy and a mono- or dialkylamino group is preferably mono- or dimethyl- or -ethylamino, i-propylamino or di-n-propylamino. The heterocyclic radicals Hc are preferably unsubstituted, or substituted by up to three methyl groups, and advantageously attached to the oxazine ring via a methylene group ($m = 1$, $q = 0$).

The moeity $C_mH_{2(m-q)}$ is either a direct bond ($m=0$), or it preferably represents methylene or ethylene; 1-propenylene or 1-propynylene respectively ($m = 3$, $q = 1$ or 2); $C_nH_{2n}$ and $C_pH_{2p}$ preferably represent $(CH_2)_n$ and $(CH_2)_p$ respectively and halogeno—$C_pH_{2p-2}$ is preferably 3-halogenoallyl. Of said integers $m$ is mainly 0 to 2 is $q$ is 0, or 3 if $q$ is 1 or 2, $n$ is mainly 1 to 3, and $p$ is mainly 2 or 3.

The acyl radicals listed for R are preferably derived from the following acids: acetic, propionic, n- or i-butyric; crotonic; cyclopropane, cyclopentane-, cyclohexane or adamantanecarboxylic; benzoic, furoic, α- or β-(fluoro, chloro, dimethylamino, diethylamino, cyclopropyl, cyclopentyl or cyclohexyl)acetic or -propionic acid.

The N-oxide is preferably the 4-N-oxide of compounds of Formula I, wherein R is lower alkyl, (cycloalkyl or Ph)—$C_mH_{2m}$ or (PhCO or carbalkoxy)—$C_nH_{2n}$, and the acid addition salts are preferably derived from the therapeutically acceptable acids listed below.

The compounds of the invention exhibit valuable pharmacological properties, for example, imipramine-type antidepressant effects. This can be demonstrated in animal tests, using advantageously mammals, such as mice, rats or monkeys, as test objects. The compounds of the invention can be applied to the animals enterally, e.g. orally, or parenterally, e.g. subcutaneously, intraperitoneally or intravenously, for example in the form of aqueous solutions or starchy suspensions. The dosage may range between about 0.1 to 100 mg/kg/day, preferably between about 1 and 75 mg/kg/day, especially between about 10 and 50 mg/kg/day. An antidepressant effect is observed, for example in the classical mouse tetrabenazine or rat reserpine ptosis tests, or preferably in the amphetamine interaction test (P. Carlton, Psychopharmacologia 1961, Vol. II, p. 364) performed with male albino rats, which are trained to press a bar every 30 seconds, in order to avoid an electric shock applied through the floor grid. In case the animals receive 0.25 mg/kg/day of amphetamine i.p., their performing rate for avoiding said shocks during a test period of about 4–5 hours is slightly higher than that of placebo (saline) treated animals. In case the animals receive the compounds of the invention (or imipramine for control purpose) in the above-mentioned doses, preferably at 20 mg/kg/day i.p. and about 45 minutes later the amphetamine, their rate of avoiding the shocks is highest, as compared with that of rats receiving (a) saline alone, (b) saline and amphetamine, or (c) the compounds of the invention and saline. The results of said tests indicate that the compounds of the invention are highly active antidepressants with a rapid onset of action and, for this purpose, also well tolerated by the intravenous route of administration. Thus, for example, administration of the 4-allyl-7,7-diphenyl-hexahydro-1,4-oxazepine, a characteristic compound of the invention, when applied intravenously as a solution of its hydrochloride in physiologic saline to dogs at an infusion rate of about 0.5 mg/kg/min. × 180 is well tolerated by the animals, especially in view of their cardiac function. Accordingly, the compounds of the invention are useful antidepressants in combatting endogenic or exogenic depressions in mammals as quickly and expediently as possible. Moreover, they are also valuable intermediates in the preparation of other useful products, especially of pharmacologically active compounds.

Particularly useful are compounds of Formula I, wherein each of alk and alk' is ethylene, R is lower alkyl, lower alkenyl, lower alkynyl, (3 to 7 ring-membered cycloalkyl, 5 to 7 ring-membered cycloalkenyl, Ph or Hc)-[$C_mH_{2(m-q)}$ or $C_mH_{2m}$-CO], (PhCO, CN, carboxy or carbalkoxy)—$C_nH_{2n}$, (hydroxy, halogeno, amino, mono- or di-lower alkylamino)—$C_pH_{2p}$, halogeno—$C_pH_{2p-2}$, or (halogeno or di-lower alkylamino)—$C_pH_{2p}$—CO, the multiple bonds in which radicals R are separated from the nitrogen atom by at least two carbon atoms, each of Ph and Ph' is phenyl, (lower alkyl)-phenyl, mono-, di- or tri-(lower alkoxy)-phenyl, (lower alkylmercapto, hydroxy, halogeno or trifluoromethyl)-phenyl, Hc is furyl, thienyl or pyridyl, unsubstituted or substituted by up to three methyl groups, $m$ is an integer from 0 to 4, $n$ such from 1 to 4, $p$ such from 2 to 4, $q$ such from 0 to 2 and $(m-q)$ is positive; or the N-oxide of the compounds wherein R is lower alkyl, (cycloalkyl or Ph)—$C_mH_{2m}$ or (PhCO or carbalkoxy)—$C_nH_{2n}$, or a therapeutically acceptable acid addition salt thereof.

Preferred compounds of the invention are those of Formula I, wherein each of alk and alk' is ethylene, R is lower alkyl, lower alkenyl, lower alkynyl, (3 to 5 ring-membered cycloalkyl, Ph, thienyl or furyl)—$C_mH_{2(m-q)}$, (PhCO, CN, carboxy or carbalkoxy)-($CH_2)_n$, (hydroxy, halogeno, amino or dialkylamino)-($CH_2)_p$ or halogeno—$C_pH_{2p-2}$, the multiple bonds in which radicals R are separated from the nitrogen atom by at least two carbon atoms, each of Ph and Ph' is phenyl, (lower alkyl)-phenyl, mono-, di- or tri-(lower alkoxy)-phenyl, (lower alkylmercapto, hydroxy, halogeno or trifluoromethyl)-phenyl, each of $m$ and $n$ is an integer from 1 to 3, $p$ such from 2 to 4, $q$ such from 0 to 2 and $(m-q)$ is positive, or a therapeutically acceptable acid addition salt thereof.

Outstanding on account of their usefulness are the compounds of Formula II

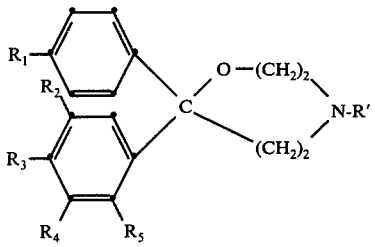

(II)

wherein R' is alkyl, alkenyl or alkynyl with up to 4 carbon atoms, the multiple bonds of which latter are separated from the nitrogen atom by at least two carbon atoms, (cyclopropyl, $R_1$-phenyl or furyl)—$C_mH_{2(m-q)}$—$CH_2$, ($R_1$-benzoyl, cyano, carboxy or carbethoxy)-($CH_2)_n$ (hydroxy, fluoro, chloro, amino or dimethylamino)-($CH_2)_p$ or chloro—$C_2H_2$—$CH_2$, $m$ is an integer from 0 to 2, $n$ such from 1 to 3, $p$ such from 2 to 3, $q$ such from 0 to 2 and $(m-q)$ is positive, $R_1$ is hydrogen, methyl, methoxy, fluoro, chloro or trifluoromethyl, each of $R_2$ to $R_5$ is hydrogen, or one thereof is methyl, fluoro, chloro or trifluoromethyl, or up to three thereof are methoxy, and the others are hydrogen, or a therapeutically acceptable acid addition salt thereof.

The most preferred compounds are those of Formula II, wherein R' is allyl, propargyl, 2-butinyl, cyclopropylmethyl or 3-chloroallyl, each of $R_1$ and $R_2$ is hydrogen, methoxy or chloro, and each of $R_3$ to $R_5$ is hydrogen, or a therapeutically acceptable acid addition salt thereof.

The compounds of this invention are prepared according to conventional methods, for example by reducing compounds of Formula III

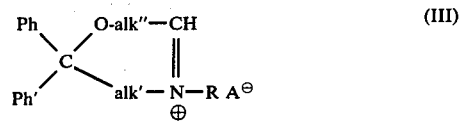

(III)

wherein alk" is lower alkylidene and A is the anion of an acid and, if desired, converting any resulting compound of Formula I into another compound of the invention.

Said reduction is advantageously carried out with catalytically activated or nascent hydrogen, e.g. hydrogen in the presence of nickel, palladium or platinum catalysts, or generated electrolytically. Also reducing agents may be used, such as simple or complex light metal hydrides, such as borones or alkali metal borohydrides or cyanohydrides, e.g. borane, or preferably sodium cyanoborohydride.

Another process for preparing the compounds of the invention consists in reducing compounds of Formula IV

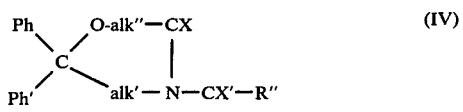

(IV)

wherein alk" is lower alkylidene, one of X and X' is $H_2$ and the other is O and R" is R without the terminal $CH_2$ and, if desired, converting any resulting compound of Formula I into another compound of the invention.

In the compounds of Formula IV the oxo group is conventionally reduced, for example with simple or complex light metal hydrides, such as borones or alkali metal aluminum hydrides, or alkoxy- or alkoxyalkoxyhydrides, e.g. diborane, lithium aluminum hydride, lithium tri-t. butoxy-aluminum hydride or sodium bis(2-methoxyethoxy)-aluminum hydride.

Finally the compounds of the invention can be prepared by adding or condensing compounds of Formulae V and VI

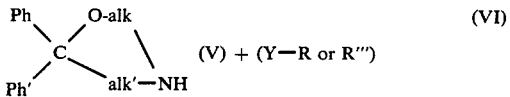

(V) + (Y—R or R''')  (VI)

or alkali salts of V, wherein Y is a reactively esterified hydroxy group, and R''' is the olefin corresponding to R with a terminal double bond, or the ethyleneoxide derived therefrom and, if desired, converting any resulting compound of Formula I into another compound or the invention.

A reactively esterified hydroxy group Y is preferably a halogen atom, advantageously chloro or bromo, or an aliphatic or aromatic sulfonyloxy group, such as alkane- or Ph-sulfonyloxy, e.g. mesyloxy, besyloxy, tosyloxy, closyloxy or brosyloxy. Condensation with R-Y is carried out at room temperature or below, or under more drastic conditions, for example at temperatures between room temperature and about 100° and/or in the presence of bases neutralizing the acids generated, such as alkali metal hydrides, hydroxides, carbonates or bicarbonates; or tert. amines, e.g. tri-lower alkylamines, pyridine or lower alkylated pyridines. The addition of the olefin R''' is advantageously carried out at room temperature or slightly raised temperatures, and/or in the presence of small amounts of hydroquinone which prevents polymerization of highly reactive olefines, e.g. acrylonitrile. The addition of said terminal ethylene oxide R''' is also carried out at room temperature or at about 50°.

In the compounds of Formula I so obtained any R may be exchanged, e.g. benzyl replaced by acyl in the reaction with a strong acyl hydride, e.g. ethyl chloroformate or cyanogen bromide. Any unsaturated R can be hydrogenated in the customary manner, advantageously with the use of catalytically activated or nascent hydrogen, as mentioned above. Cyano-$C_nH_{2n}$-compounds can similarly be reduced to $H_2N—C_{n+1}H_{2n+2}$ compounds and primary amines obtained mono- or di-alkylated with said reactive esters of lower alkanols, or by reductive alkylation, or acylated with such reactive derivatives of said acids (acyl halides or anhydrides). Any resulting tert. amines sufficiently stable against oxidants, can be converted into N-oxides, for example, by treating them with suitable oxidation agents, such as hydrogen peroxide, aliphatic or aromatic percarboxylic acids, e.g. peracetic or perbenzoic acid.

Any resulting base can be converted into a corresponding acid addition salt, preferably with the use of a therapeutically useful acid anion exchange preparation, or resulting salts can be converted into the corresponding free bases, for example, with the use of a base, such as a metal hydroxide, basic salt, ammonia, amino or cation exchange preparation, e.g. an alkali metal hydroxide or carbonate. Said acid addition salts are preferably such of therapeutically acceptable inorganic or organic acids, such as strong metalloidic acids, for example hydrohalic, e.g. hydrochloric or hydrobromic acid; sulfuric, phosphoric, nitric or perchloric acid; aliphatic or aromatic carboxylic sulfonic acids, e.g. formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, 4-aminosalicylic, pamoic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfamic acid. These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The starting material of Formula III can be prepared from the corresponding acyclic amino-aldehydes, which are generated in acidic media from their open or cyclic acetals, e.g. diethyl or ethylene acetals, which in turn are obtained by reacting corresponding $\beta$-hydroxy-$\beta$,$\beta$-diphenyl-propionitriles with reactive esters of glyoxal acetals, reducing the resulting ether with said complex aluminum hydrides and treating said resulting acyclic amino-aldehydes with HA, e.g. an inorganic acid listed below.

The compounds of Formula IV are prepared either by condensing the sec. amines (Ph, Ph')=C(OH)—alk'—NH—R with reactive derivatives of glycolic acids, e.g. chloroacetyl chloride, or by reacting compounds of Formula V with R''—CO halides. Said compounds of Formula V are similarly obtained as those of Formula III, wherein R is hydrogen, either as salt or free Schiff's base.

In case mixtures of geometrical or optical isomers of the compounds of Formulae I to V are obtained, these can be separated into the single isomers by methods in themselves known, e.g. by fractional distillation, crystallization and/or chromatography. Racemic products can likewise be resolved into the optical antipodes, for example, by separation of diastereomeric salts thereof, e.g. by the fractional crystallization of d- or l-tartrates.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably at the boiling point of the solvents used, at atmospheric or superatmospheric pressure.

The invention further includes any variant of the present process, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being especially valuable, e.g. those of Formula II.

The pharmacologically active compounds of the invention are useful in the manufacture of pharmaceutical compositions comprising an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods respectively and contain about 0.1 to 75%, preferably about 1 to 50%, of the active ingredient.

The following examples are intended to illustrate the invention and are not to be construed as being limitations thereon. Temperatures are given in degrees Centrigrade, and all parts wherever given are parts by weight. If not mentioned otherwise, all evaporations are performed under reduced pressure, preferably between about 15 and 100 mm Hg.

EXAMPLE 1

17.8 g of 4-benzyl-3-oxo-7,7-diphenyl-hexahydro-1,4-oxazepine are added portionwise to the suspension of 2.28 g of lithium aluminum hydride in 300 ml of diethyl ether while stirring and cooling with an ice-bath. The mixture is allowed to warm up to room temperature and refluxed for 3½ hours. Then it is cooled with ice and 2.3 ml of water, 2.3 ml of 15% aqueous sodium hydroxide are added, followed by 6.9 ml of water. The suspension is filtered, the precipitate washed three times with 50 ml of hot methylene chloride, the combined filtrates dried, filtered and evaporated. The residue is taken up in acetone, the solution acidified with hydrogen chloride and diluted with diethyl ether, to yield the 4-benzyl-7,7-diphenyl-hexahydro-1,4-oxazepine hydrochloride melting at 243°–244° (the regenerated free base melts at 129°–131°).

Analogously the following free bases of Formula II are prepared from equivalent amounts of the coresponding starting materials: R′=benzyl

| No. | $R_1$ | $R_2$ | $R_3$ | $R_4$ | $R_5$ | m.p.° C |
|-----|-------|-------|-------|-------|-------|---------|
| 1 | H | H | H | H | $OCH_3$ | 129–131 |
| 2 | H | $OCH_3$ | H | H | H | 78–80 |
| 3 | H | $PCH_3$ | $OCH_3$ | $OCH_3$ | H | 142–144 |
| 4 | H | Cl | H | H | H | 127–128 |
| 5 | F | H | F | H | H | 121–123 |

The starting material is prepared as follows:

The solution of 8.2 g of acetonitrile in 200 ml of tetrahydrofuran is added dropwise to the solution of 14.08 g of butyl lithium in 125 ml of tetrahydrofuran and 125 ml of n-hexane while stirring at −70° under nitrogen and stirring is continued for 1 hour. Thereupon the solution of 36.4 g benzophenone in 200 ml of tetrahydrofuran is added dropwise and the mixture stirred for 20 minutes at room temperature. It is poured onto 300 g of ice and 100 ml of 3N hydrochloric acid, the organic layer separated and the aqueous phase extracted three times with 50 ml of diethyl ether. The combined organic solutions are dried, evaporated and the residue recrystallized from ethanol, to yield the β-hydroxy-β,β-diphenyl-propionitrile melting at 136°–138°.

Analogously the nitriles corresponding to compounds No. 1 to 5 are prepared from equivalent amounts of the respective starting materials. They melt at 118°–120°, 75°–80°, 131°–133°, 86°–90° and 82°–87° respectively.

35.5 g of β-hydroxy-β,β-diphenyl-propionitrile are added portionwise to the stirred suspension of 12.9 g of lithium aluminum hydride in 800 ml of diethyl ether while cooling with an ice bath. After stirring for 15 hours at room temperature and 2 hours at the boil, it is cooled again and 12.9 ml of water, 12.9 ml of 15% aqueous sodium hydroxide and 38.7 ml of water are added in this order. The mixture is filtered, the residue washed 3 times with 150 ml of methylene chloride, the filtrate dried, evaporated and the residue recrystallized from ethanol, to yield the 3-hydroxy-3,3-diphenyl-propylamine melting at 134°–136°.

Analogously the amines corresponding to compounds No. 1 to 5 are prepared from equivalent amounts of the respective starting materials. They melt at 119°–122°, not above room temperature, 68°–72°, 72°–76° and 102°–107° respectively.

To the solution of 58.0 g of 3-hydroxy-3,3-diphenylpropylamine in 700 ml of methylene chloride and 30.5 g of pyridine, that of 37.5 g of benzoyl chloride in 300 ml of methylene chloride is added dropwise during 2 hours while stirring and cooling with an ice-bath. Stirring is continued for 1 hour at 0°–5°, the mixture washed twice with 200 ml of N hydrochloric acid, 150 ml of 5% aqueous sodium hydroxide and 25 ml of water each, dried, evaporated and the residue triturated with diethyl ether, to yield the N-benzoyl-3-hydroxy-3,3-diphenylpropylamine melting at 140°–141°.

Analogously the amides corresponding to compounds No. 1,2,4 and 5 are prepared from equivalent amounts of the respective starting materials. They melt at 102°–104°, 132°–135°, 94°–96° and 144°–145° respectively.

72.3 g of N-benzoyl-3-hydroxy-3,3-diphenylpropylamine are added portionwise to the suspension of 16.3 g of lithium aluminum hydride in 1.6 lt of diethyl ether while stirring and cooling with an ice-bath. The mixture is stirred for 2 hours while warming to room temperature and 3 hours while refluxing. It is cooled again and 16.3 g of water, 16.3 ml of 15% aqueous sodium hydroxide and 49 ml water are added in this order, filtered and the residue washed 3 times with 300 ml of warm chloroform. The combined filtrates are dried and evaporated, to yield the N-benzyl-3-hydroxy-3,3-diphenylpropylamine melting at 145°–146°.

Analogously the amines corresponding to compounds No. 1,2,4 and 5 are prepared from equivalent amounts of the respective starting materials. They melt at 97°–100°, 60°–63°, 102°–104° and 97°–100° respectively.

These compounds can also be prepared as follows:

To the stirred mixture of 133.4 g of 3-hydroxy-3,3-diphenylpropylamine, 36 g of anhydrous magnesium sulfate and 250 ml of methylene chloride, the solution of 15.6 g of benzaldehyde in 50 ml of methylene chloride is added. The suspension is stirred for 15 hours at room temperature, heated to the boil and filtered. The residue is washed 3 times with 100 ml of methylene chloride, the combined filtrates evaporated and the residue recrystallized from ethanol, to yield the corresponding cyclic Schiff's base, i.e. the 2,6,6,-triphenyl-tetrahydro-1,3-oxazine melting 163°–165°.

The mixture of 21.4 g thereof, 800 ml of anhydrous ethanol, containing 2.42 g of hydrogen chloride, and 3.0 g of 10% palladium on carbon is hydrogenated at room temperature and atmospheric pressure until the theoretical amount of hydrogen has been absorbed. It is filtered, the filtrate evaporated and the residue recrystallized from ethanol, to yield the N-benzyl-3-hydroxy-3,3-diphenylpropylamine melting at 146°–148°.

Analogously the N-benzyl-3-hydroxy-3-phenyl-3-(3,4,5-trimethoxyphenyl)-propylamine is prepared, melting at 108°–111°.

To the stirred solution of 15.6 g of N-benzyl-3-hydroxy-3,3-diphenylpropylamine in 7.0 g of di-isopropylethylamine and 150 ml of methylene chloride, that of 5.88 g of chloroacetyl chloride in 50 ml of methylene chloride is added dropwise while stirring and cooling with an ice-bath. Thereupon the solution is stirred for 15 minutes at 0°–5° and washed successively with N hydrochloric acid, 10% aqueous sodium bicarbonate and finally with saturated aqueous sodium chloride. The organic layer is separated, dried, filtered and evaporated, to yield the N-benzyl-N-chloroacetyl-3-hydroxy-3,3-diphenylpropylamine showing in the I.R.-spectrum a strong band at 1640 cm$^{-1}$.

Analogously the starting materials corresponding to compounds No. 1 to 5 are prepared from equivalent amounts of the respective starting materials. Their main I.R.-bands are the following: 1644, 1645, 1650, 1650 and 1642 cm$^{-1}$ respectively.

The compounds listed in the above table are the: 4-benzyl-7-phenyl-(o- or m-methoxyphenyl, 3,4,5-trimethoxyphenyl or m-chlorophenyl)-hexahydro-1,4-oxazepines and the 4-benzyl-7,7-di-(p-fluorophenyl)-hexahydro-1,4-oxazepine respectively.

The solution of 19.3 g of N-benzyl-N-chloroacetyl-3-hydroxy-3,3-diphenylpropylamine in 150 ml of dimethylformamide is added dropwise to the suspension of 1.2 g of sodium hydride in 50 ml of dimethylformamide while stirring and cooling with an ice-bath. The mixture is allowed to warm up to room temperature, stirred for 15 hours and evaporated. The residue is partitioned between 150 ml methylene chloride and 50 ml of N hydrochloric acid, the organic layer separated, washed with water, dried, filtered and evaporated. The residue is triturated with diethyl ether and recrystallized from ethanol, to yield the 4-benzyl-3-oxo-7,7-diphenyl-hexahydro-1,4-oxazepine of the formula

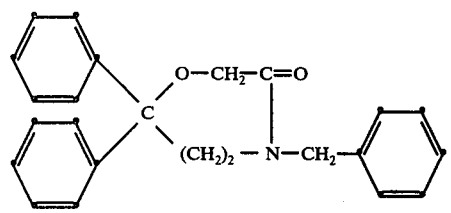

melting at 185° to 186°.

Analogously the following compounds of Formula IV are prepared from equivalent amounts of the corresponding starting materials: X=O, CX'—R″ = benzyl, alk″ = CH$_2$, alk' = (CH$_2$)$_2$

| No. | Ph | Ph' | m.p.° C |
|---|---|---|---|
| 1 | C$_6$H$_5$ | 2-CH$_3$O—C$_6$H$_4$ | 93–95 |

-continued

| No. | Ph | Ph' | m.p.° C |
|---|---|---|---|
| 2 | " | 3-CH$_3$O—C$_6$H$_4$ | 127–129 |
| 3 | " | 3,4,5-(CH$_3$O)$_3$—C$_6$H$_2$ | 154–156 |
| 4 | " | 3-Cl—C$_6$H$_4$ | 177–178 |
| 5 | 4-F—C$_6$H$_4$ | 4-F—C$_6$H$_4$ | 147–149 | i.e. the 4-benzyl-3-oxo-7-phenyl-(o- or m-methoxyphenyl, 3,4,5-trimethoxyphenyl or m-chlorophenyl)-hexahydro-1,4-oxazepines and the 4-benzyl-3-oxo-7,7-di-(p-fluorophenyl)-hexahydro-1,4-oxazepine respectively.

EXAMPLE 2

To the stirred solution of 5.06 g of 7,7-diphenyl-hexahydro-1,4-oxazepine in 50 ml of methylene chloride, 2.6 g of allyl bromide are added, followed by 40 ml of 10% aqueous sodium bicarbonate and the mixture is stirred for 24 hours at room temperature. The organic layer is separated, washed with water, dried, filtered and evaporated. The residue is taken up in acetone, the solution acidified with hydrogen chloride in acetone and diluted with diethyl ether, to yield the 4-allyl-7,7-diphenyl-hexahydro-1, 4-oxazepine hydrochloride melting at 246° to 247°.

Analogously the following compounds of Formula II are prepared from equivalent amounts of the corresponding starting materials: R$_1$ = H

| No. | R' | R$_2$ | R$_3$ | R$_4$ | R$_5$ | Salt | m.p.° C |
|---|---|---|---|---|---|---|---|
| 1 | CH$_3$ | OCH$_3$ | OCH$_3$ | OCH$_3$ | H | HCl | 208–209 |
| 2 | allyl | " | " | " | H | " | 232–233 d. |
| 3 | " | " | H | H | H | " | 199–201 d. |
| 4 | " | Cl | H | H | H | " | 243–245 |
| 5 | " | F | H | F | H | " | 255–256 |
| 5a | " | H | H | H | OCH$_3$ | " | 240–242 d. |
| 6 | (CH$_3$)$_2$C=CH—CH$_2$ | H | H | H | H | " | 239–240 d. |
| 7 | propargyl | H | H | H | H | " | 229–231 d. |
| 8 | " | OCH$_3$ | H | H | H | " | 187–189 |
| 9 | " | Cl | H | H | H | " | 218–220 |
| 10 | CH$_3$—C≡C—CH$_2$ | H | H | H | H | " | 217–219 |
| 11 | △—CH$_2$ | H | H | H | H | " | 268–270 |
| 12 | 2-phenethyl | H | H | H | H | cyclamate | 159–161 |
| 13 | C$_6$H$_5$—C≡C—CH$_2$ | H | H | H | H | HCl | 105–110 |
| 14 | furfuryl | H | H | H | H | " | 240–242 d. |
| 15 | furfuryl | OCH$_3$ | H | H | H | " | 167–170 d. |
| 16 | C$_2$H$_5$—CO—CH$_2$ | H | H | H | H | " | 193–195 |
| 17 | Cl—CH=CH—CH$_2$ | H | H | H | H | " | 261–263 |
| 18 | " | OCH$_3$ | H | H | H | " | 174–177 d. |
| 19 | " | Cl | H | H | H | " | 223–225 d. |

Said compounds are the hydrochlorides of the 4-methyl or allyl 7-phenyl-7-(3,4,5-trimethoxyphenyl)-hexahydro-1,4-oxazepines, the 4-allyl-7-phenyl-7-(3-methoxy-, 3-chloro-, (3,5-difluoro- or 2-methoxyphenyl)-hexahydro-1,4-oxazepines, the 4- 3-methyl-but-2-enyl)- or propargyl-7,7-diphenyl-hexahydro-1,4-oxazepines, the 4-propargyl-7-phenyl-(3-methoxy or 3-chlorophenyl)-hexahydro-1,4-oxazepines, the 4-(but-2-ynyl or cyclopropylmethyl)-7,7-diphenylhexahydro-1,4-oxazepines, the cyclamate of the 4-(2-phenethyl)-7,7-diphenyl-hexahydro-1,4-oxazepine and the hydrochlorides of the 4-(3-phenyl-prop-2-ynyl- or furfuryl)-7,7-diphenyl-hexahydro1,4-oxazepines, the 4-furfuryl-7-phenyl-7-(3-methoxyphenyl)hexahydro-1,4-oxazepine, the 4-[2-oxobutyl or 3-chloroallyl)-7,7-diphenyl-hexahydro-1,4-oxazepines and the 4-(3-chloroallyl)-7-phenyl-7-(3-methoxy- or 3-chlorophenyl)-hexahydro-1,4-oxazepines.

The starting material is prepared as follows:

To the solution of 11.15 g of 3-hydroxy-3,3-diphenyl-propionitrile, 13.4 g of iodo acetaldehyde diethylacetal, and 0.9 g of tetra-n-butylammonium hydrogen sulfate in 40 ml of methylene chloride, 10 ml of 50% aqueous sodium hydroxide are added and the mixture is well stirred at room temperature for 24 hours. It is washed with water, dried and evaporated, to give the 2-(2-cyano-1,1-diphenylethoxy)-acetaldehyde diethylacetal as an oil which is sufficiently pure to be used without purification.

The solution of 6.8 g thereof in 100 ml of diethyl ether is added dropwise to the stirred suspension of 1.15 g of lithium aluminum hydride in 20 ml of diethyl ether, while cooling with ice. Upon completion of the addition, the mixture is stirred under reflux for 6 hours. It is cooled and excess hydride is destroyed by successive addition of 1.15 ml of water, 1.15 ml of 15% aqueous sodium hydroxide and 3.45 ml more water. The mixture is filtered, the filtrate is dried and evaporated to give the oily 2-(3-amino-1,1-diphenylpropoxy)-acetaldehyde diethylacetal.

5.15 g thereof are dissolved in 60 ml of 95% ethanol and 10 ml of 6N hydrochloric acid are added. The solution is stirred at 40°–45° for 3 hours, cooled and 0.5 g of 10% palladium on charcoal are added. The mixture is hydrogenated at 2.7 atm. and 40° until the hydrogen uptake ceases. It is filtered, the filtrate neutralized with aqueous sodium hydroxide and evaporated. The residue is partitioned between water and methylene chloride, the organic phase is separated, dried and evaporated. The residue is dissolved in the minimum amount of acetone, the solution neutralized with acetonic cyclohexylsulfamic acid and the precipitate collected, to yield the 7,7-diphenyl-hexahydro-1,4-oxazepine cyclamate melting at 161°–163°.

EXAMPLE 3

To the solution of 30.25 g of 4-benzyl-7,7-diphenyl-hexahydro-1,4-oxazepine in 300 ml of methylene chloride, that of 10.4 g of ethyl chloroformate in 100 ml of methylene chloride is added dropwise while stirring. After 30 minutes the mixture is allowed to warm up to room temperature and stirred for 15 hours. It is successively washed twice with 50 ml of N hydrochloric acid, 50 ml of N aqueous sodium hydroxide and 50 ml of saturated sodium chloride each, dried, filtered and evaporated. The residue is recrystallized from hexane, to yield the 4-carbethoxy-7,7-diphenylhexahydro-1,4-oxazepine melting at 122° to 123°.

EXAMPLE 4

The mixture of 3.20 g of 7,7-diphenyl-hexahydro-1,4-oxazepine, 2.54 g of 4-chloro-4'-fluoro-butyrophenone, 3.35 g of anhydrous potassium carbonate and 0.21 g of sodium iodide is refluxed for 22 hours, while stirring. The suspension is cooled, filtered, the filtrate evaporated and the residue dissolved in acetone. The solution is acidified with ethereal hydrogen chloride, to yield the 4-[3-(4-fluorobenzoyl)-propyl]-7,7-diphenylhexahydro-1,4-oxazepine hydrochloride melting at 137°–140°.

Analogously the 4-(4'-chlorobenzoylmethyl)-7,7-diphenyl-hexahydro-1,4-oxazepine hydrochloride is prepared, melting at 102°–104°.

EXAMPLE 5

The mixture of 6.5 g of 7,7-diphenyl-hexahydro-1,4-oxazepine, 1.2 g of ethylene oxide, 0.5 ml of water and 20 ml of methanol is stirred at 40°–45° for 4 hours and at 50° for 2½ hours. It is cooled, the precipitate formed, filtered off and recrystallized from benzene-hexane, to yield the 4-(2-hydroxyethyl)-7,7-diphenyl-hexahydro-1,4-oxazepine melting at 122°–123° (its hydrochloride melts at 190°–192°).

EXAMPLE 6

The solution of 22.2 g of 7,7-diphenyl-hexahydro-1,4-oxazepine and 0.2 g of hydroquinone in 50 ml of acrylonitrile is refluxed for 18 hours, cooled and evaporated. The residue is taken up in chloroform, the mixture filtered through a short column of silica gel, eluted with chloroform and the eluate evaporated. The residue is recrystallized from ethanol, to yield the 4-(2-cyanoethyl)-7,7-diphenyl-hexahydro-1,4-oxazepine melting at 106°–107°.

EXAMPLE 7

3.06 g of 4-(2-cyanoethyl)-7,7-diphenyl-hexahydro-1,4-oxazepine are added portionwise to the suspension prepared by combining the solution of 1.33 g of anhydrous aluminum chloride in 30 ml of diethyl ether with that of 0.38 g of lithium aluminum hydride in 30 ml of diethyl ether while stirring and cooling with an ice-bath. The mixture is allowed to warm up to room temperature, stirred for 5 ½ hours and cooled again to 0°–5°. Thereupon 5 ml of water and 15 ml of 3N aqueous sulfuric acid are added and the organic layer extracted with 3N aqueous sulfuric acid. The aqueous layers are combined, made basic with concentrated aqueous sodium hydroxide and the mixture extracted four times with 15 ml of diethyl ether each. The extract is dried, filtered and evaporated. The residue is taken up in ethanol and the solution acidified with ethereal hydrogen chloride, to yield the 4-(3-aminopropyl)-7,7-diphenyl-hexahydro-1,4-oxazepine dihydrochloride melting at 190°–192° with decomposition.

EXAMPLE 8

To the solution of 6.2 g of 4-(3-aminopropyl)-7,7-diphenyl-hexahydro-1,4-oxazepine in 60 ml of acetonitrile, 8.4 ml of 37% aqueous formaldehyde are added while stirring and keeping the mixture at room temperature. Thereupon 2.0 g of sodium cyanoborohydride are added portionwise and after 15 minutes glacial acetic acid is added so that the pH of the solution is maintained at about 7. The solution is stirred for 45 minutes at said pH and evaporated. The residue is taken up in 80 ml of 2N aqueous potassium hydroxide, the mixture extracted three times with 50 ml of diethyl ether each, the extract washed with 0.5 N aqueous potassium hydroxide and re-extracted thrice with 40 ml of N hydrochloric acid each. The acidic extract is made basic with solid potassium hydroxide, extracted thrice with 50 ml of diethyl ether each, the extract dried, filtered and evaporated. The residue is taken up in ethanol and the solution acidified with ethereal hydrogen chloride, to yield the 4-(3-dimethylaminopropyl)-7,7-diphenylhexahydro-1,4-oxazepine dihydrochloride melting at 269°–271° with decomposition.

EXAMPLE 9

7.0 g of 4-carbethoxy-7,7-diphenyl-hexahydro-1,4-oxazepine (Example 3) are added portionwise to the suspension of 0.90 g of lithium aluminum hydride in 80 ml of diethyl ether while stirring and cooling with ice. The mixture is allowed to warm up to room temperature, refluxed for 6 hours and again cooled to 0° to 5°. Thereupon 0.9 ml of water, 0.9 ml of 15% aqueous sodium hydroxide and 2.7 ml of water are added in this order, the mixture is filtered, the filtrate dried and evaporated. The residue is taken up in acetone and the solution acidified with cyclohexylsulfamic acid in acetone, to yield the 4-methyl-7,7-diphenyl-hexahydro-1,4-oxazepine melting at 199° to 201°.

Analogously the 4-(cyclopropylmethyl, phenethyl and furfuryl)-7,7-diphenyl-hexahydro-1,4-oxazepine hydrochlorides are prepared from the corresponding amides prepared according to Example 10; they are identical with those obtained according to Example 2.

EXAMPLE 10

To the solution of 4.5 g of 7,7-diphenyl-hexahydro-1,4-oxazepine and 2.65 g of di-isopropyl-ethylamine in 30 ml of methylene chloride, that of 2.21 g of chloroacetyl chloride in 25 ml of methylene chloride is added dropwise while stirring and cooling with ice. After stirring for 30 minutes at 0°–5°, the mixture is washed twice with 10 ml of cold N hydrochloric acid and 10 ml of cold 10% aqueous sodium carbonate each, dried, filtered and evaporated. The residue is triturated with diethyl ether and recrystallized from ethanol, to yield the 4-(2-chloroacetyl)-7,7-diphenyl-hexahydro-1,4-oxazepine melting at 150°–152°.

The solution of 5.0 g thereof in 20 ml of methylene chloride is added to that of 1.85 g of dimethylamine in 40 ml of methylene chloride and the mixture stirred for 5 hours at room temperature. It is washed with 2N aqueous sodium hydroxide, dried, filtered and evaporated. The residue is dissolved in acetone and the solution acidified with ethereal cyclohexylsulfamic acid, to yield the 4-(2-dimethylamino-acetyl)-7,7-diphenyl-hexahydro-1,4-oxazepine cyclamate melting at 183°–185°.

The analogously prepared 4-(cyclopropylcarbonyl and 2-furoyl)-7,7-diphenyl-hexahydro-1,4-oxazepines melt at 185°–187° and 261°–263° respectively.

EXAMPLE 11

To the solution of 2.5 g of 7,7-diphenyl-hexahydro-1,4-oxazepine in 5 ml of dimethylformamide, 1.5 g of anhydrous potassium carbonate are added while stirring, followed by the dropwise addition of the solution of 0.85 g of chloroacetonitrile in 2 ml of dimethylformamide and the suspension is stirred for 5 hours at room temperature. It is poured onto a mixture of ice and water, the aqueous phase extracted twice with 20 ml of diethyl ether each, the extract dried, filtered and evaporated. The residue is recrystallized from ethanol, to yield the 4-cyanomethyl-7,7-diphenyl-hexahydro-1,4-oxazepine melting at 119°–121° (its hydrochloride melts at 178°–180° with decomposition).

EXAMPLE 12

To the stirred solution of 5.0 g of 4-(3-aminopropyl)-7,7-diphenyl-hexahydro-1,4-oxazepine and 2.0 g of triethylamine in 20 ml of methylene chloride, that of 3.2 g of adamantane-1-carboxylic acid chloride in 15 ml of methylene chloride is added while cooling to 0°. The mixture is stirred at said temperature for 15 minutes, washed with 2N aqueous sodium hydroxide, water, dried and evaporated. The residue dissolved in acetone, the solution acidified with cyclohexylsulfamic acid and the mixture diluted with diethyl ether, to yield the 4-[3-(1-adamantylcarboxamido)-propyl]-7,7-diphenyl-hexahydro-1,4-oxazepine cyclamate melting at 138°–140°.

EXAMPLE 13

The mixture of 11.2 g of 7-(4-hydroxyphenyl)-7-phenylhexahydro-1,4-oxazepine hydrochloride, 110 ml of dry acetonitrile. 14.0 g of triethylamine and 5.05 g of allyl bromide is stirred at room temperature for 48 hours. It is evaporated and the residue partitioned between benzene and 2N aqueous sodium hydroxide. The aqueous layer is separated, combined with a further basic extraction of the benzene solution, and the combined aqueous solutions are adjusted to 9 pH of 4–6.3 with acetic acid. The solid which separates is collected, dried and converted to the hydrochloride in acetone (mp. 150°–153°). The free base is liberated again and crystalized from ethanol, to yield the 4-allyl-7-(4-hydroxyphenyl)-7-phenyl-hexahydro-1,4-oxazepine melting at 205°–207°.

The starting material is prepared according to the method illustrated by Example 1, yielding the following intermediates:

(a) β-hydroxy-β-(4-benzyloxyphenyl)-β-phenyl-propionitrile, mp. 102°–104°;
(b) 3-hydroxy-3-(4-benzyloxyphenyl)-3-phenyl-propylamine, mp. 122°–124°;
(c) N-benzoyl-3-hydroxy-3-(4-benzyloxyphenyl)-3-phenyl-propylamine, showing an I.R. band at 1638 cm$^{-1}$;
(d) N-benzyl-3-hydroxy-3-(4-benzyloxyphenyl)-3-phenyl-propylamine, mp. 98°–100°.
(e) N-benzyl-N-chloroacetyl-3-hydroxy-3-(4-benzyloxyphenyl)-3-phenyl-propylamine, showing an I.R. band at 1648 cm$^{-1}$;
(f) 4-benzyl-3-oxo-7-(4-benzyloxyphenyl)-7-phenyl-hexahydro-1,4-oxazepine, mp. 111°–113° and
(g) 4-benzyl-7-(4-benzyloxyphenyl)-7-phenyl-hexahydro-1,4-oxazepine, mp. 93°–96°.
(h) The solution of 7.0 g thereof in 140 ml of 95% ethanol is hydrogenated over 0.7 g of 10% palladium on charcoal at atmospheric pressure and room temperature until the hydrogen uptake ceases. The catalyst is filtered off, the solvent evaporated, the residue taken up in the minimum amount of acetone and the solution acidified with hydrogen chloride, to yield the 7-(4-hydroxyphenyl)-7-phenyl-hexahydro-1,4-oxazepine hydrochloride melting at 211°–213°.

EXAMPLE 14

The solution of 6.0 g of 2-(3-cyclopropylmethylamino-1,1-diphenylpropoxy)-acetaldehyde diethyl acetal in 60 ml of 95% ethanol and 10 ml of 6N hydrochloric acid is stirred at 20°–45° for 3 hours, cooled and 0.5 g of 10% palladium on charcoal are added. The mixture is hydrogenated at 2.7 atm. and 40° until the hydrogen uptake ceases. It is filtered, the filtrate neutralized with aqueous sodium hydroxide and evaporated. The residue is partitioned between water and methylene chloride, the organic phase separated, dried and evaporated. The residue is taken up in the minimum amount of acetone, the solution acidified with hydrogen chloride and diluted with diethyl ether, to yield the 4-cyclopropylmethyl-7,7-diphenyl-hexahydro-1,4-oxazepine hydrochloride melting at 268°–270°; it is identical with compound No. 11 of Example 2.

The starting material is prepared as follows. The solution of 3.4 g of 2-(3-amino-1,1-diphenylpropoxy)-acetaldehye diethyl acetal, 1.5 g of triethylamine and 35 ml of methylene chloride is stirred and cooled in an ice bath during the dropwise addition of the solution of 1.05 g of cyclopropane carboxylic acid chloride in 15 ml of methylene chloride. Upon stirring subsequently for ½ hour at 0°–5° C, the solution is washed successively with 2N aqueous sodium hydroxide and saturated aqueous sodium chloride, dried and evaporated, to yield the 2-(3-cyclopropylcarbonylamino-1,1-diphenylpropoxy)-acetaldehyde diethyl acetal.

The solution of 3.3 g thereof in 30 ml of benzene is added dropwise to the stirred suspension of 0.5 g of lithium aluminum hydride in 40 ml of diethyl ether while cooling with ice. The mixture is stirred at room temperature for 18 hours, then cooled and treated with 0.5 ml of water, 0.5 ml of 15% aqueous sodium hydroxide and 1.5 ml more water. It is filtered, the filtrate dried and evaporated, to give the 2-(3-cyclopropylmethylamino-1,1-diphenylpropoxy)-acetaldehyde diethyl acetal.

EXAMPLE 15

Preparation of 10,000 tablets each containing 50.0 mg of the active ingredient:

| Formula: | |
|---|---|
| 4-allyl-7,7-diphenyl-hexahydro-1,4-oxazepine hydrochloride | 500.00 g |
| Lactose | 1,706.00 g |
| Corn starch | 90.00 g |
| Polyethylene glycol 6,000 | 90.00 g |
| Talcum powder | 90.00 g |
| Magnesium stearate | 24.00 g |
| Purified water | q.s. |

Procedure

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 100 mg of the active ingredient.

| Formula: | |
|---|---|
| 4-allyl-7,7-diphenyl-hexahydro-1,4-oxazepine hydrochloride | 1,000.0 g |
| Lactose | 2,800.0 g |
| Talcum powder | 200.0 g |

Procedure

All the powders are passed through a screen with openings of 0.6 mm. Then the drug substance is placed in a mixer and mixed first with the talcum, then with the lactose until homogeneous. No 1 gelatin capsules are filled with 400 mg each, using a filling machine.

Analogously tablets or capsules of the other compounds of the invention are prepared, preferably of those corresponding to Formula II and being illustrated by the previous examples.

I claim:

1. A compound of the formula

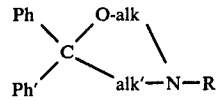

wherein each of alk and alk' is ethylene, R is (PhCO or CN) -$C_nH_{2n}$; each of Ph and Ph' is phenyl, unsubstituted or substituted by up to three members of lower alkyl, lower alkoxy, lower alkylmercapto, hydroxy, halogeno or trifluoromethyl; and $n$ is an integer from 1 to 4; or a therapeutically acceptable acid addition salt thereof.

2. A compound as claimed in claim 1, in which formula each of alk and alk' is ethylene, R is (PhCO or CN)-$C_nH_{2n}$, each of Ph and Ph' is phenyl, (lower alkyl)-phenyl, mono-, di- or tri-(lower alkoxy)-phenyl, alkylmercapto, hydroxy, halogeno or trifluoromethyl)-phenyl, and $n$ is an integer from 1 to 4, or a therapeutically acceptable acid addition salt thereof.

3. A compound as claimed in claim 1, in which formula each of alk and alk' is ethylene, R is (PhCO or CN)-$(CH_2)_n$, each of Ph and Ph' is phenyl, (lower alkyl)-phenyl, mono-, di- or tri-(lower alkoxy)-phenyl, (lower alkylmercapto, hydroxy, halogeno or trifluoromethyl)-phenyl, and $n$ is an integer from 1 to 3, or a therapeutically acceptable acid addition salt thereof.

4. A compound as claimed in claim 1 and corresponding to the formula

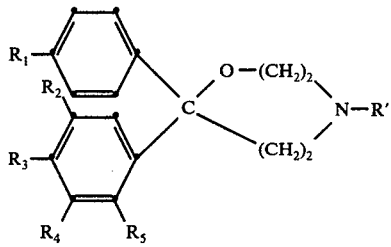

wherein R' is ($R_1$-benzoyl or cyano)-$(CH_2)_n$, $n$ is an integer from 1 to 3, $R_1$ is hydrogen, methyl, methoxy, fluoro, chloro or trifluoromethyl, each of $R_2$ to $R_5$ is hydrogen, or one thereof is methyl, fluoro, chloro or trifluoromethyl, or up to three thereof are methoxy, and the others are hydrogen, or a therapeutically acceptable acid addition salt thereof.

5. A compound as claimed in claim 1 and being the 4-[3-(4-fluorobenzoyl)-propyl]-7,7-diphenyl-hexahydro-1,4-oxazepine or the hydrochloride thereof.

6. A compound as claimed in claim 1 and being the 4-(4'-chlorobenzoylmethyl)-7,7-diphenyl-hexahydro-1,4-oxazepine or the hydrochloride thereof.

* * * * *